(12) United States Patent
Lemieux (10) Patent No.: US 10,781,694 B2
(45) Date of Patent: Sep. 22, 2020

(54) POLYGON BASED, MAXIMUM VALUE PIT DESIGN SYSTEM AND METHOD

(71) Applicant: Marc Lemieux, Sanford, NC (US)

(72) Inventor: Marc Lemieux, Sanford, NC (US)

(73) Assignee: Marc Lemieux, Sanford, NC (US)

( * ) Notice: Subject to any disclaimer, the term of this patent is extended or adjusted under 35 U.S.C. 154(b) by 222 days.

(21) Appl. No.: 15/242,058

(22) Filed: Aug. 19, 2016

(65) Prior Publication Data

US 2017/0053044 A1     Feb. 23, 2017

Related U.S. Application Data

(60) Provisional application No. 62/207,668, filed on Aug. 20, 2015.

(51) Int. Cl.
*E21C 41/26*     (2006.01)
*G01V 99/00*     (2009.01)
(Continued)

(52) U.S. Cl.
CPC .............. *E21C 41/26* (2013.01); *G01V 11/00* (2013.01); *G01V 99/005* (2013.01); *G01N 33/24* (2013.01); *G06Q 50/02* (2013.01)

(58) Field of Classification Search
CPC ...... E21C 41/26; G01V 99/005; G01V 11/00; G06Q 50/02; G01N 33/24
(Continued)

(56) References Cited

U.S. PATENT DOCUMENTS 7,519,515 B2 * 4/2009 Froyland ................. E21C 41/26
299/19
8,600,708 B1 * 12/2013 Mallet ..................... G06T 17/05
703/2

OTHER PUBLICATIONS

Lizotte, Yves. "The economics of computerized open-pit design. International Journal of Surface Mining, Reclamation and Environnnent";2.2 (1988). 59-78. (Year: 1988).*

(Continued)

*Primary Examiner* — Kamini S Shah
*Assistant Examiner* — John E Johansen
(74) *Attorney, Agent, or Firm* — Coats & Bennett, PLLC (57) ABSTRACT

A system and method for pit design that that operates directly on a geological model without creating a three dimensional block model thereby minimizing modeling dilution. A resource in a deposit may be divided into a set of base resource units that closely conform to the resource geometry and value distribution and that can be mined by the equipment assumed to perform the excavation. A resource increment (RI) is defined by a base resource unit and any resource and waste over the base resource unit which is assumed to be excavated in conformance with slope stability and safe practices forming an approximation of a truncated inverted cone. A systematic sorting and grouping process of the RIs iterates down a list of RIs and identifies RIs and/or RI groups that add value to the pit while excluding RIs and/or RI groups that do not add value. The sorting and grouping process operates on the recognition that, for RIs analyzed later in the RI list, the cost of intersections of waste overlaying the RIs base resource unit is carried by RIs analyzed earlier in the list. The sorting and grouping process allows intersecting RIs to be evaluated, grouped into RI groups, and either included or not included in the pit so that a maximum valued pit is defined. One aspect of the novel sorting and grouping process is the identification and grouping of interdependent RIs and RI groups. Another novel aspect of this pit design system is the application of over lapping RI bases with size defined large enough to represent the minimal accessible mining space for the equipment proposed. Larger sized bases should lead to reduction in the complexity of intersecting RIs and computational time. The end result is a model of the pit including a list of RIs and/or RI groups to include in the pit and resource and/or reserve statements.

12 Claims, 4 Drawing Sheets

(51) Int. Cl.
*G01N 33/24* (2006.01)
*G01V 11/00* (2006.01)
*G06Q 50/02* (2012.01)

(58) Field of Classification Search
USPC .................................................... 703/1, 10
See application file for complete search history.

(56) References Cited

OTHER PUBLICATIONS

Gu, Xiao-Wei, W. A. N. G. Qing, and G. E. Shu. "Dynamic phase-mining optimization in open-pit metal mines." Transactions of Nonferrous Metals Society of China 20.10 (2010). pp. 1974-1980. (Year: 2010).*
Sides, E. J. "Geological modelling of mineral deposits for prediction in mining." Geologische Rundschau 86.2 (1997). pp. 342-353. (Year: 2010).*
Bakhtavar, Eezzaddin, Koroush Shahriar, and Kazem Oraee. "A model for determining optimal transition depth over from open-pit to underground mining." Proceedings of 5th International Conference on Mass Mining, Luleå, Sweden. 2008. pp. 1-8. (Year: 2008).*
Building Block | Definition of Building Block by Merriam-Webster. 2019. pp. 2-3. (Year: 2019).*
Lizotte, Yves. "The economics of computerized open-pit design." International Journal of Surface Mining, Reclamation and Environment. 2.2 (1988). 59-78. (Year: 1988).*

* cited by examiner

POLYGON BASED, MAXIMUM VALUE PIT DESIGN SYSTEM AND METHOD

RELATED APPLICATION

The present application claims priority to U.S. Provisional Application Ser. No. 62/207,668, filed 20 Aug. 2015, the disclosure of all of which is expressly incorporated by reference herein in its entirety.

TECHNICAL FIELD

The present disclosure relates generally to mining and, more particularly to systems and methods for the design of surface mine pits.

BACKGROUND

The purpose of mining a resource is to make as much money as possible within legal, ethical, safety, environmental, social economic and technical constraints. This requires mapping the economically recoverable resources (ore) so that the mine planning can identify the distribution of value in the deposit and mine it in a sequence that maximizes the deposit value. One of the basic surface mine planning tools used to help map the distribution of values based on the geological model is referred to by mine planners as an "optimizer", i.e. a computing system used to define a pit that has maximum value for a given set of inputs. The "optimizer" is more correctly referred to as a pit design tool, system, process or method. Current state of the pit design tools define maximum valued pits in a mineral deposit for a given set of inputs based on a three dimensional array of profit values representing blocks in a deposit which are determined to be either in or out of the pit. The value at each array point represents a block of mineral and/or waste material having common dimensions.

Unfortunately, geology generally doesn't usually conform to the block geometry of regular arrays used in conventional optimizers. Relatively large blocks may not adequately represent complex geology, segregate valuable resource from waste, model variable pit wall slopes or replicate mining constraints. The result is crudely positioned pit walls and less well defined resource and reserve statements. The quality of the pit design may be improved by reducing block size. For example, in the case of deposits having faults, dykes, sills, multiple seams, or veins with variable thickness and inclination, smaller blocks may be required in order to avoid significant modeling dilution. Modeling dilution occurs when waste and the valuable material are included in a block resulting in an average value for the block and not a separation of value based on the separation of the components. Also, the slope of the excavations required to safely recover the resource is generally better represented by smaller block sizes. However, reducing block size exponentially increases the number of blocks that need to be processed and the computational complexity of the pit design process. Current optimizers using models with small blocks may include resources in pit bottoms inaccessible by proposed mining equipment. The available maximum value optimizers are not able to identify and follow footwall seams or incorporate minimum size pit bottom during the execution of non-heuristic algorithms.

SUMMARY

Figure 1:
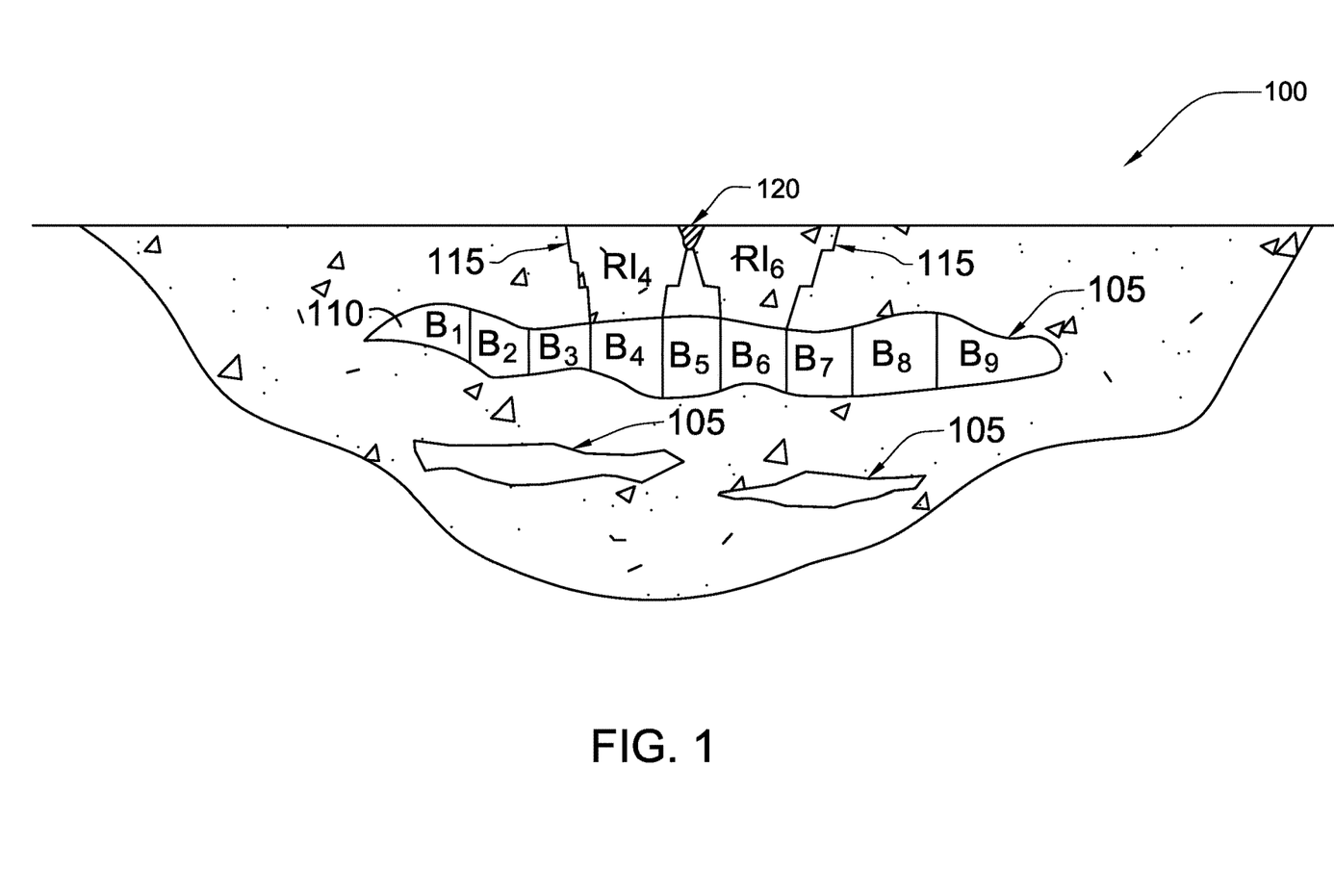
FIG. 1 is a schematic diagram illustrating a resource deposit in a pit divided into base resource units.

The present disclosure relates to systems and methods for identifying an excavation (pit) which theoretically has a boundary of equal value and all the resource within that boundary having a value equal to or greater than the value at the boundary. The systems and methods herein described may operate directly on a geological model of a deposit as represented in FIG. 1 without definition of a block model, avoiding the limitations of a block model. In the systems and methods described herein, pre-defined block models may be replaced by gridded seam, triangulated, isopleth or polygon based models that can conform to the geology of the resource 105 thus minimizing modeling dilution.

The minimum sized unit of resource applied to the geological model that a mining method and equipment assumed for the mine plan can excavate is defined in this application as a resource volume FIG. 1 $b_1$ to $b_9$. The resource volume is defined by a polygon at its base on a mining level, seam base or some other structure. The upper surface of a resource volume can similarly be define by an overlaying mining level, top of seam or other structure. A resource volume maybe overlain by waste material and/or other resource volumes. The excavation of a resource volume and the overlaying waste and/or resource volume must conform to the safe slope requirements dictated by geotechnical criteria slope stability and safety. Slopes are protected upward from the base resource units in a form approximating the shape of a truncated inverted cone to generate resource increments (RIs) that extend upward through the geological model and faithfully honor slope constraints without being restricted to the geometry of a block model. The RI is constructed to either an initial topographic surface or a surface created by the assumed mining of overlaying resource and waste volumes. The base resource volume and the overlaying material is referred to as a resource increment (RI). The content and value of an RI can be calculated and reported.

By superimposing polygon-based RIs on the geological model, the deposit may be divided into a set of base resource units that closely conform to the geology of the deposit. Each base resource unit represents a minable chunk of the resource deposit that if excavated and processed would yield a salable product.

An initial list of RIs is defined and ordered from the top of the deposit to the bottom. A systematic sorting and grouping process iterates down the list and identifies RIs and/or RI groups that add value to the pit while excluding RIs and/or RI groups that do not add value. The sorting and grouping process operates on the recognition that, for RIs analyzed later in the RI list, the cost of intersections of waste and value of resource overlaying the RIs base resource unit is attributed to RIs analyzed earlier in the list. The sorting and grouping process allows intersecting RIs to be evaluated, grouped into RI groups, and either included or not included in the pit so that a maximum valued pit is defined. One aspect of the novel sorting and grouping process is the identification and grouping of interdependent RIs and RI groups. The end result is a model of the pit including a list of RI and/or RI groups to include in the pit The systems and methods facilitates the application of large RI base resource units defining minimum required working space pit bottoms without modeling dilution while overlapping the base elements to provide accurate pit wall positioning. Large base resource units minimize RI intersection complexity and significantly reduce the computational complexity of designing a maximum valued pit compared to a block model with small sized blocks using Learchs-Grossman or maximum flow algorithms. The footwall following capability can be programmed and dealt with by the algorithm. A preprocessor can segregate out RIs that will definitely not be included in a pit designed for a given set of inputs reducing clutter and computational complexity in the sorting and grouping process. A value centered procedure to generate the initial list of RIs can improve performance. All these capabilities will reduce the time to produce pits that more reliably reflect the geology and mining constraints while minimizing post process smoothing of pit design as currently required. Reporting of resources and reserves required by regulatory authorities can be developed with more confidence.

DETAILED DESCRIPTION

Referring now to the drawings, FIG. 1 illustrates a deposit 100 containing a resource 105. The resource 105 in this example comprises a seam containing mineral that may to be mined if economical. In open pit mining, the ore or mineral contained in the resource 105 is extracted by excavating the material overlaying the resource. In order to maximize the profitability of the pit, it is desirable to minimize the volume of waste material that must be removed in order to extract the valuable resource.

For purposes of explanation, the resource 105 is shown as being divided into base resource volumes 110 denominated $b_1$-$b_9$. A base resource volume 110 represents a minable unit of the resource 105. Only a portion of the resource 105 is shown as being divided in FIG. 1. FIG. 1 also illustrates two resource increments (RIs) 115. A RI 115 comprises a base resource volume 110 along with a cone of material projecting upward from base resource volume 110 to the surface of the pit. The RIs 115 contain overlaying waste and/or resource that needs to be excavated to recover the base resource volume. Two RIs denominated as $RI_4$ and $RI_6$ are shown. As can be seen in FIG. 1, $RI_4$ and $RI_6$ overlap and the intersection 120 is shown by cross-hatching. While only two RIs are shown in FIG. 1, those skilled in the art will appreciate that all of the resource 105 to be mined will be divided into base resource volumes and that corresponding RIs will be created for each base resource volume.

Figure 2:
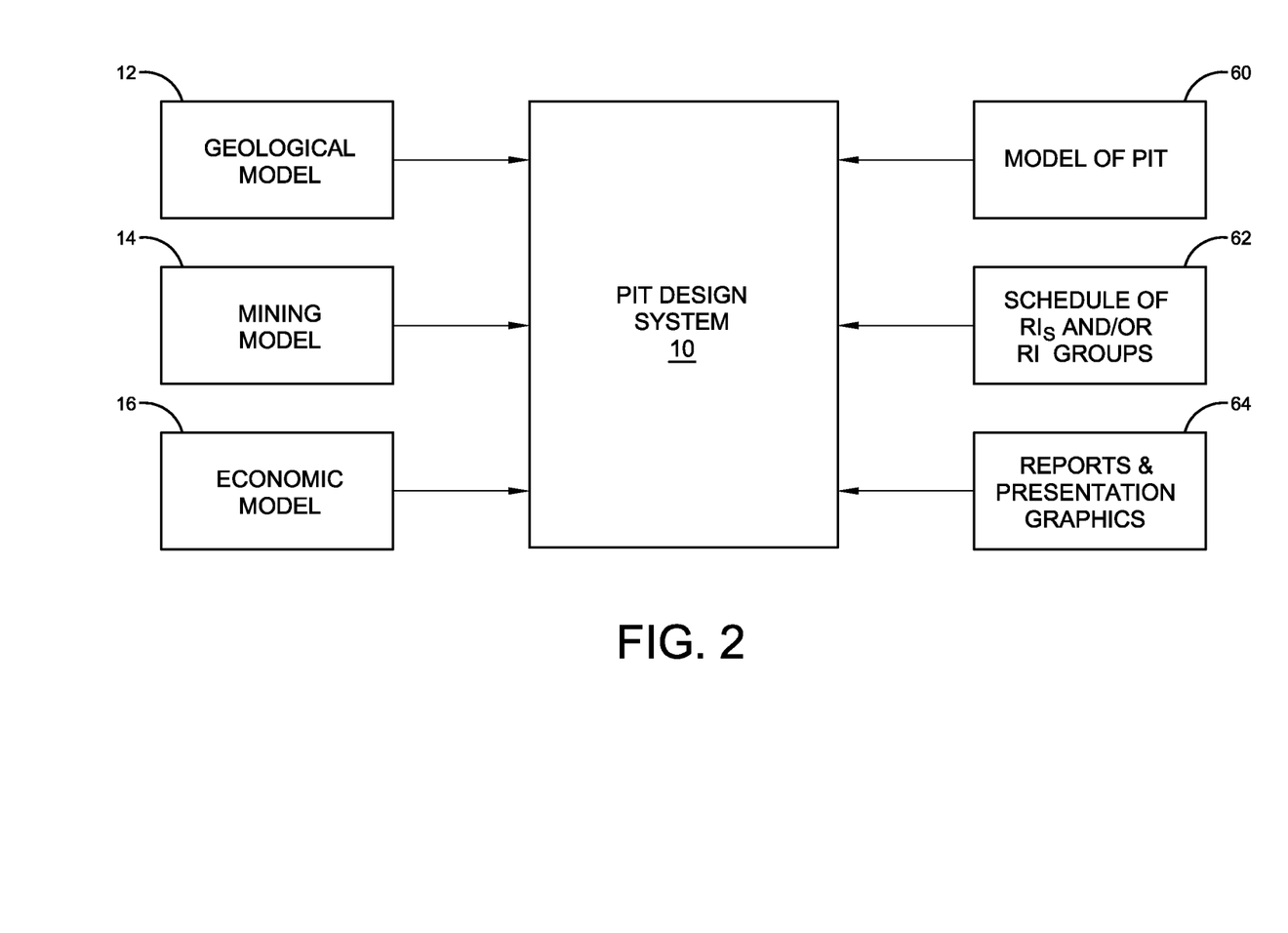
FIG. 2 is a block diagram of a pit design system as herein described.

FIG. 2 is a block diagram of a pit design system 10 for optimizing the output of a pit to maximize the profit. To maximize the pit value, the pit design system 10 performs an pit design procedure, which may be divided into three basic processes:
1. the initialization process;
2. the resource increment listing process; and
3. the sorting and grouping process.

During the initialization process, the pit design system 10 receives input that is used during the pit design process to design a maximum-valued pit. Exemplary input parameters to the pit design system 10 comprise geological models 12, mining models 14, and economic models 16 used in the pit design process. The geological model 12 contains information about the geology and topography of the area where the pit is located. The mining model 14 provides the slope constraints for the pit wall definition and pit geometry based in part on mining equipment selection assumptions. The economic model 16 provides information about the value of resources contained in the pit and the cost of removing waste excavating and processing the resource. The various input models used by the pit design system 10 are described in more detail in § 1 and § 2 of the attached Appendix, which is part of this application.

During the RI listing process, the pit design system 10 generates a list of resource increments (RIs) that may be potentially excavated to mine the resource. Each RI represents a chunk of the resource to be mined, referred to herein as a base resource unit, along with the overlaying material that needs to be excavated to recover the base resource unit. The definition of the RIs is based on the geological model, the geotechnical constraints and mining requirements. The pit design system 10 also calculates a value to each RI in the RI list. The generation of the RI list and the calculation of values to RIs is described in more detail in §§ 4-16 of the attached Appendix. Commercially available software for RI definition and list generation includes Carlson's Mining software, Maptek's Vulcan software, and Dassault's System's Minex and Surpac software.

To define the RIs, the pit design system 10 divides the resource in the geological model received during initialization into base resource units, which are referred to in the Appendix as base volumes. In the example shown in FIG. 1, the resource seam closest to the surface of the pit is analyzed by defining nine base resource volumes 110 denominated $b_1$-$b_9$ on the seam. For ease of explanation, only the uppermost deposit is shown as being divided. Those skilled in the art will appreciate that, in practice, each seam in deposit 100 would be analyzed by superimposing contiguous base resource units on the seam as represented by $b_1$-$b_9$.

In the example shown in FIG. 1, each base resource unit is overlain by waste material and/or other base resource units. The excavation of a base resource unit and the overlying waste and/or base resource units must conform to the safe slope requirements for pit walls dictated by geotechnical criteria, slope stability, and safety. These constraints are derived from the geological and mining models. Therefore, to define the RIs, the pit design system 10 extends a cone upwardly through the overlaying material from each base resource unit to an assumed surface of the pit. Referring back to FIG. 1, two RIs are illustrated extending upward from base resource units $b_4$ and $b_6$b6. While only two RIs are illustrated, it is understood that an RI will be generated for each base resource unit.

The initial list of RIs is generated beginning at the top of the deposit and moving downward in the order of base elevation. The value of each RI is calculated based on geological and economic model. As each RI is constructed and evaluate the topographic surface is assume to be modified to reflect the excavation of the RI. In computing the value of each RI, it is assumed that the earlier RIs in the list have been removed so that the cost of removing intersecting material is borne by the RI earlier in the list. The RI list will have a mix of values. Some RI values will be greater than or equal to 0 indicating that the RI adds value to the pit, while others will be less than 0 indicating that the RI does not add value to the pit. The final RI list will comprise of a set of ordered pairs given by (R, V) where R points to the base polygon of the RIs so a RI can be reconstructed as required by the algorithm and V is its calculated value.

After the initial RI list is generated, the pit design system 10 begins the sorting and grouping process. The sorting and grouping process is described in §§ 17-40 in the attached Appendix. The main purpose of the sorting and grouping procedure is to identify and differentiate RIs or RI groups that add value to the pit from the RIs or RI groups that do not add value to the pit. The RI list is partitioned into two sets, denoted as set A and set B. See, Appendix, § 17. At the end of the sorting and grouping process, set A comprises a list of RIs or RI groups that add value to the pit while set B comprises a list of RIs or RI groups that do add value to the pit. RIs or RI groups adding value to the pit are included in the final pit design.

One aspect of the sorting and grouping procedure is the grouping of individual RIs into RI groups. The term RI group as used herein is defined as a set of one or more RIs which will after grouping will be treated as a single RI. At the start of the sorting and grouping process, there is a one-to-one correspondence between RIs and RI groups. That is, a group is defined for each RI in the initial RI list including only that RI. As will be explained in greater detail below, during the sorting and grouping procedure, two or more RI groups may be combined to from a larger RI group.

Figure 3:
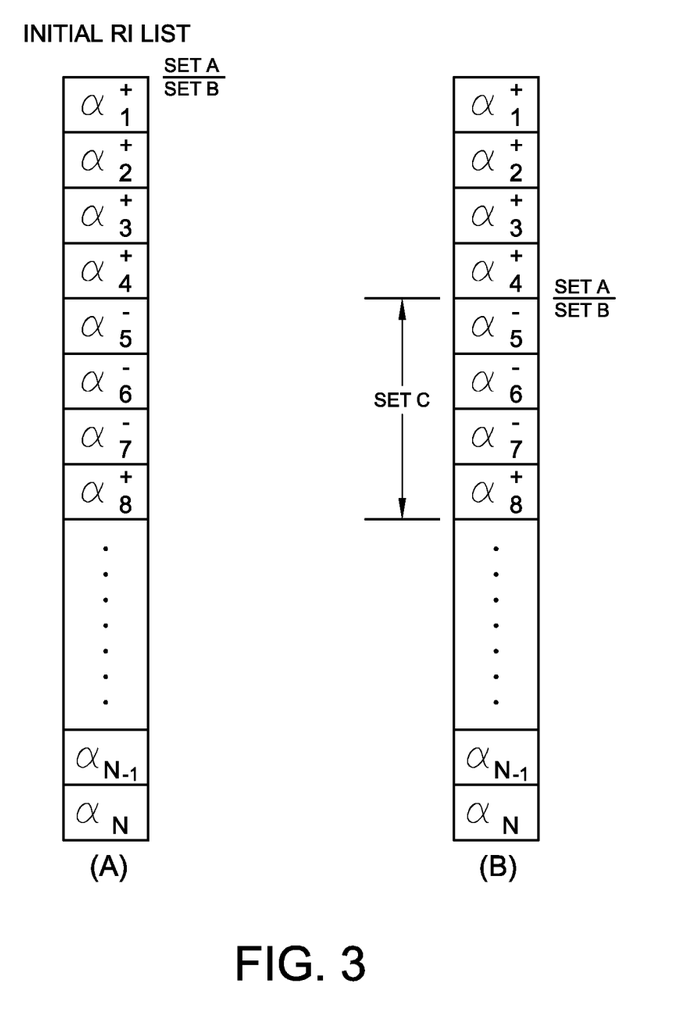
FIG. 3 is a schematic diagram illustrating the sorting and grouping process using by the pit design system.
Figure 4:
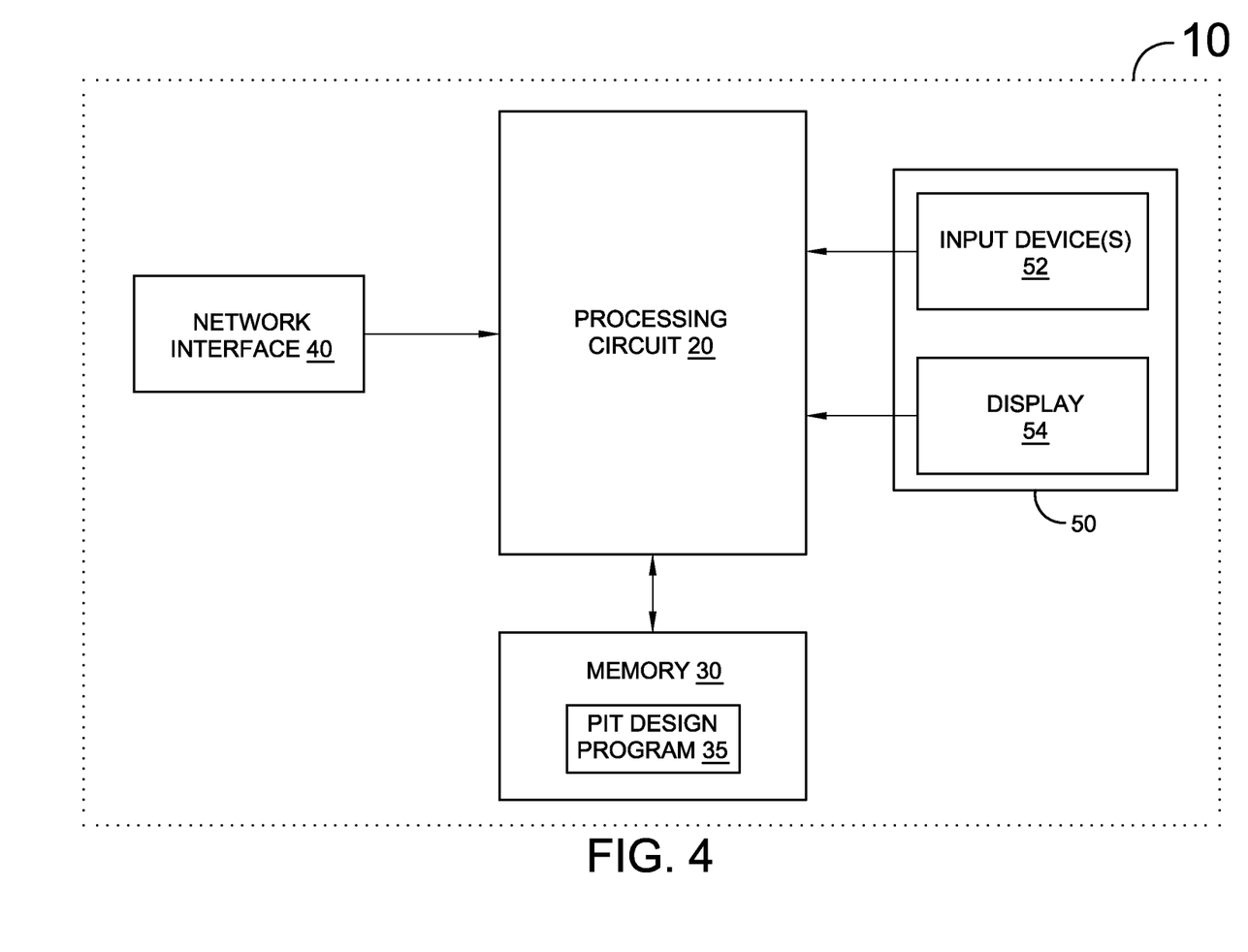
FIG. 4 is a more detailed functional block diagram of the pit design system.

At the start of the sorting and grouping process, all RI groups belong to set B, which contains RI groups that do not add value to the pit, or are yet to be evaluated. During the sorting and grouping process, the pit design system 10 sequentially processes the RI groups in the RI list and assigns RI groups that add value to the pit to set A. One unique aspect of the sorting and grouping procedure described herein is the method of differentiating RI groups that should be included in set A from RI groups that should be excluded from set A. The pit design system 10 starts with the first RI group in set B. If the first listed RI group in set B has a positive value, it is moved from set B to set A. When a RI group is moved from set B to set A, the process continues with the next RI group. Whenever a RI group in the first position in set B has a positive value, it is moved to set A. Eventually, the sorting and grouping process will reach a point where the first RI group in set B has a negative value. In this case, the sorting process is temporarily halted and a resorting/grouping procedure is performed. After the resorting/grouping procedure is performed, the sorting and grouping process is resumed. The sorting and grouping continues until two conditions are met: (1) no RI or RI group in set A can, if removed from set A, increase the value of set A; and (2) no RI or RI group remains in set B that can add value to set A FIG. 3 illustrates the sorting and grouping procedure. FIG. 3a shows the initial RI list with the partition between set A and set B at the top of the RI list. At this point, all RI groups, which are denoted by the Greek symbol α, belong to set B. The superscript for each RI group indicates whether the RI group has a positive value or a negative value. In this example, the first four RI groups, $\alpha_1$-$\alpha_4$, have a positive value. FIG. 3b illustrates the RI list after four iterations or cycles of the sorting and grouping process. At this point, the pit design system has processed the first four RI groups and moved the partition between set A and set B to between α4 and α5. As seen in FIG. 3, the next three RI groups, $\alpha_6$-$\alpha_7$, are negative. The first positive RI group in set B is $\alpha_8$. At this point, the pit design procedure performs the resorting/grouping procedure.

The reordering/grouping procedure is described in §§ 30-39 in the Appendix. To briefly summarize, to begin the resorting/grouping procedure, the pit design system 10 begins the reordering/grouping procedure by defining a set C comprising the first positive valued RI group in set B and all negative valued RI groups that are listed before the first positive RI group. See, Appendix, § 24. In the example shown in FIG. 3b, set B comprises three negative valued RI groups, $\alpha_6$-$\alpha_7$ followed by a positive valued RI group, $\alpha_8$. In this case, set C is defined to include $\alpha_6$-$\alpha_8$. After set C is defined, the pit design system 10 stores the members of set C in set C' for future reference and repeatedly reorders the RI groups in set C to identify an interdependent set of RI groups in set C. Reordering is performed by moving the RI group with value equal to or greater than zero in the last position in set C to the first position and shifting the other RI groups down. Set C is part of set B so B is reordered, by reordering set C. Each time set B is reordered, a new set C is defined and compared to set C'.

In creating the RI list, the cost and value associated with mining any intersecting material, i.e., material shared by two or more intersecting RI groups, is assumed to be carried by the earlier RI groups. By changing the order of RIs in set C, the cost and value of excavating the intersecting material will be reallocated from one RI group to another. Therefore, the values assigned to the RI groups need to be recalculated upon reordering.

During the reordering process, the pit design system 10 repeatedly reorders the RI groups in set C by moving the last RI group in set C to the first position. There are three possible outcomes from reordering the RI groups in set C. First, set C may comprise only independent RI groups having no intersections. Independent RI groups are described in § 31 of the Appendix. In this case, reordering the RI groups in set C will not change the value of any RI group. In this case, the positive valued resource group, after being moved to the top of list B, will be moved to list A and the resorting/grouping procedure will end. Processing will return to the main sorting and grouping procedure. In the previous example, if RI groups $\alpha_5$-$\alpha_8$ are independent, $\alpha_8$ will be moved to the first position in set B and processing returns to the main sorting and grouping process. Because $\alpha_8$ is positive, the pit design system 10 will move $\alpha_8$ to set A and the sorting and grouping process processing will continue as before.

The second possible outcome is that set C may comprise two or more sequentially dependent RI groups. Sequentially dependent RI groups are described in § 32 of the Appendix. Because sequentially dependent RI groups share intersecting material, reordering the RI groups changes their value. In this scenario, one or more RI groups initially valued equal to or greater than zero in set C become a negative RI group but none of the negative RI groups become valued greater than or equal to zero. Alternatively, one or more RI groups with initial value greater or equal to zero remains valued greater or equal zero and one or more negative valued RI groups value changes to greater than or equal to zero. In this scenario, the membership of set C will change after reordering. In the case of sequentially dependent RI groups, the last RI group in set C will stay positive after being moved to the first position, or the last RI group will turn negative and another RI group not in the last position in set C turns positive. In either case, the reordering/grouping procedure will terminate and processing will return to the main sorting and grouping procedure.

The third possible outcome is that set C comprises a set of interdependent RI groups as described in § 33 of the Appendix. Set C may contain some independent negatively valued Ris In this case, after one minus the number of RI groups in C repeated reordering of the RI groups in set C be moved to the last position in C and require a redefinition of set C where independent negative RI are rejected from C, On additional reordering the first RI group in set C will always be negative and the last RI group will always be positive. Also, the total value of the RI groups in set C will be always positive or always negative, but will not change from positive to negative, or vice versa on additional reordering. This condition identifies the RI groups in set C as interdependent. In this case, the interdependent RI groups may be grouped together into a larger RI group. After creating the new RI group, the processing returns to the main sorting and grouping procedure.

The sorting and grouping process continues until the following conditions are satisfied:
1) no resource group in set A can, if removed from set A, increase the value of set A; and
2) no resource group in set B can, if added to the set A, increase value of set A;

At the end of the sorting and grouping process, the RI groups in set A define the final pit. The pit design system 10 may, among other things, may generate a 3D model 60 of the final pit, generate a list 62 of the RIs and/or RI groups in the final pit, and generate reports and presentation graphics 64. In some embodiments, the pit design system may also perform a parametric analysis of defining pits with successively lower unit valued resource.

Further details of the pit design method are described in the Appendix. The Appendix divides the pit design method into five procedures. Procedure 1, which corresponds to the initialization process and RI list generation process described above, sets up the geological model, economic model, mining assumptions and all other required inputs. Procedures 2-5 correspond to the sorting and grouping process described above. Procedure 2 is the main control loop for the sorting and grouping process. Procedure 3 is used to assign a positive RI or RI grouping in the first position of set B to set A. Procedure 4 terminates the pit design process if there are no more positive RIs or RI groupings in set B. Procedure 5 illustrates the reordering/grouping procedure.

The pit design system 10 may be implemented by a computing device running any known operating system, such as Windows, Linux, OSX, or Unix. FIG. 3 illustrates the main functional components of a pit design system 10 configured to implement the pit design process as herein described. The pit design system 10 comprises a processing circuit 20, memory 30, network interface 40, and user interface 50. The processing circuit 20 may comprise one or more microprocessors, microcontrollers, hardware circuits, firmware, or a combination thereof. The processing circuit 20 controls the operation of the pit design system 10 according to programs stored in memory 30 and performs the pit design methods described herein and in the accompanying Appendix. In the latter case, the programs may include application programming interface (APIs) to enable information sharing between the programs. Also, interprocess communication (IPC) protocols may be used to enable sharing of information between programs.

Memory 30 may comprise both volatile and non-volatile memory. Program instructions and data needed for operation may be stored in a non-volatile memory, such as read only memory (ROM), flash memory, or other non-volatile memory devices. Volatile memory, such as random access memory (RAM) may be used to store temporary data. The memory 30 may be implemented as one or more discrete devices, stacked devices, or integrated with the processing circuit 20. Memory stores a pit design program 35 that, when executed by the processing circuit 20, causes the pit design system to perform the pit design methods as herein described.

Network interface 40 comprises an interface circuit for communicating with remote devices over a communication network. The network interface 40 may provide connection to both wired and wireless networks. In one embodiment, the network interface 40 comprises an Ethernet interface for connecting the computing device to a wired network. In other embodiments, the network interface 40 may comprise a wireless interface circuit, such as a Wi-Fi or wireless LAN (WLAN) interface.

User interface 50 includes an input device 52 and display 54. The input device 52 and display 54 enables the user to interact with the pit design system 10. Input device 52 may, for example, comprise a key pad, mouse, other pointing device, or touchpad. The input device or devices 52 allow the user to input commands and data during the operation of the pit design system 10. Display 54 allows the user to see graphical user interfaces and information that is output by the computer programs. In some embodiments, the display 54 may comprise a touch screen display that also functions as a user input device 52.

What is claimed is:

1. A method implemented by a pit design system to maximize a value of a pit excavated in a mining operation, said method comprising:
   (a) receiving into the processing system a geological model representing resources to be mined;
   (b) dividing, by the pit design system, resources in the geological model into base resource units;
   (c) generating, by the pit design system based on the defined base resource units and the geological model, a set of resource increments to excavate the base resource units, each resource increment comprising a base resource unit and overlaying material approximating an inverted truncated cone extending upward from the base resource unit to a surface of the pit or the surface reflecting the excavation of all previously processed resource increments;
   (d) defining, by the pit design system, a set of resource increment groups, each of which includes one or more resource increments;
   (e) determining, by said pit design system, a group value for each resource increment group based on an order of excavation;
   (f) defining a set B of resource increment groups sorted based on the order of excavation; and
   (g) iteratively processing the resource increment groups in set B in sorted order by:
   1. when a first positive-valued resource increment group in set B is in a first position in set B, moving the resource increment group in the first position to a second set A and continuing another iteration of processing;
   2. when the first positive-valued resource increment group in set B is not in the first position:
      a. defining a subset C of consecutive resource increment groups beginning with the resource increment group in a first position in set B and ending with the first positive-valued resource increment group in set B;
      b. reordering the resource increment groups in subset C a predetermined number of times depending on a size of the subset C by cyclically shifting a resource increment group in a last position in subset C to a first position in subset C;
      c. during each reordering, recomputing the values of the resource increment groups in subset C;
      d. identifying, in the reordered subset C, two or more interdependent resource increment groups based on the recomputed values of the resource increment groups, wherein at least one interdependent resource increment groups has a positive value;

e. combining the interdependent resource increment groups into a new resource increment groups; and f. computing a value of the new resource increment group;

g. redefining subset C after each reordering, wherein the redefined subset C comprises one of:
   i. a positive value resource increment group in the first position in set B;
   ii. a group of consecutive resource increment groups beginning with a negative resource increment group in the first position in set B and ending with the first positive value resource increment group; or
   iii. a group of consecutive resource increment groups beginning with a negative resource increment group in the first position in set B and ending with the first positive value resource increment group followed by one or more trailing positive value resource increment groups within the previously defined subset C;

h. terminating the reordering when membership in subset C changes; and i. continuing another iteration of processing, when membership in subset C does not change.

2. The method of claim 1 wherein at least one of the interdependent resource increment groups has a negative value.

3. The method of claim 1 wherein dividing, by the pit design system, resources in the geological model into a plurality of base resource volumes comprises generating said base resource volumes using a polygon to define the resource volume base.

4. The method of claim 3 wherein said base resource volumes are generated directly from the geological model without a predefined block model.

5. The method of claim 3 wherein generating said base resource volumes using a polygon-base for the base resource volume comprises, for each base resource unit:
   generating, a base polygon as a lower bounding surface of the base resource unit;
   generating an upper bounding surface of the base resource unit; and
   generating sides of the base resource unit to conform to safe mining constraints as specified in said mining model.

6. The method of claim 1 wherein the one or more interdependent resource increment groups are identified after a predetermined number of cyclic shifts.

7. A pit design system to maximize a value of a pit excavated in a mining operation, said pit design system comprising:
   an interface circuit to receive input parameters including a geological model representing resource in the deposits to be mined; and
   a processing circuit configured to process the geological model to maximize the pit value for a given set of economic inputs, said processing circuit being configured to:
   (a) receive into the processing system a geological model representing resources to be mined;
   (b) divide, by the pit design system, resources in the geological model into base resource units;
   (c) generate, by the pit design system based on the defined base resource units and the geological model, a set of resource increments to excavate the base resource units, each resource increment comprising a base resource unit and overlaying material approximating an inverted truncated cone extending upward from the base resource unit to a surface of the pit or the surface reflecting the excavation of all previously processed resource increments;
   (d) define, by the pit design system, a set of resource increment groups, each of which includes one or more resource increments;
   (e) determining, by said pit design system, a group value for each resource increment group based on an order of excavation;
   (f) defining a set B of resource increment groups sorted based on the order of excavation; and
   (g) iteratively process the resource increment groups in set B in sorted order by:
      1. when a first positive-valued resource increment group in set B is in a first position in set B, moving the resource increment group in the first position to a second set A and continuing another iteration of processing;
      2. when the first positive-valued resource increment group in set B is not in the first position:
         a. define a subset C of consecutive resource increment groups beginning with the resource increment group in a first position in set B and ending with the first positive-valued resource increment group in set B;
         b. reorder the resource increment groups in subset C a predetermined number of times depending on a size of the subset C by cyclically shifting a resource increment group in a last position in subset C to a first position in subset C;
         c. during each reordering, recompute the values of the resource increment groups in subset C;
         d. identify, in the reordered subset C, two or more interdependent resource increment groups based on the recomputed values of the resource increment groups, wherein at least one interdependent resource increment group has a positive value;
         e. combine the interdependent resource increment groups into a new resource increment groups; and
         f. compute a value of the new resource increment group;
         g. redefine subset C after each reordering, wherein the redefined subset C comprises one of:
            i. a positive value resource increment group in the first position in set B;
            ii. a group of consecutive resource increment groups beginning with a negative resource increment group in the first position in set B and ending with the first positive value resource increment group; or
            iii. a group of consecutive resource increment groups beginning with a negative resource increment group in the first position in set B and ending with the first positive value resource increment group followed by one or more trailing positive value resource increment groups within the previously defined subset C;
         h. terminate the reordering when membership in subset C changes; and
         i. continue another iteration of processing when membership in subset C does not change.

8. The pit design system of claim 7 wherein at least one of the interdependent resource increment group has a negative value.

9. The pit design system of claim 7 wherein the processing circuit is further configured to generate said base resource volumes using a polygon to define the resource volume base.

10. The pit design system of claim 9 wherein the processing circuit is further configured to generate the base resource volumes directly from the geological model without a predefined block model.

11. The pit design system of claim 9 wherein generating said base resource volumes using a polygon for the base resource volume comprises, for each base resource unit:
   generate, a base polygon as a lower bounding surface of the base resource unit;
   generate an upper bounding surface of the base resource unit; and
   generate sides of the base resource unit to conform to safe mining constraints as specified in said mining model.

12. The pit design system of claim 7 wherein the processing circuit is configured identify the to one or more interdependent resource increment groups after a predetermined number of cyclic shifts.

* * * * *